| United States Patent [19]
Kobayakawa et al.

[11] 4,016,276
[45] Apr. 5, 1977

[54] TREATMENT OF LIVER DYSFUNCTION WITH 2-AMINO-6-BENZYL-3-ETHOXYCARBONYL-4,5,6,7-TETRAHYDRO-THIENO[2,3-C]PYRIDINE HYDROCHLORIDE

[75] Inventors: Toshihiro Kobayakawa, Yoshitomi; Hiroshi Yasuda, Nakatsu; Kazuhiro Goto, Nakatsu; Michio Nakanishi, Nakatsu, all of Japan

[73] Assignee: Yoshitomi Pharmaceutical Industries, Ltd., Osaka, Japan

[22] Filed: Apr. 17, 1975

[21] Appl. No.: 569,118

[52] U.S. Cl. .............................................. 424/256
[51] Int. Cl.² ..................................... A61K 31/435
[58] Field of Search .................................... 424/256

[56] References Cited
UNITED STATES PATENTS 3,563,997  2/1971  Nakanishi et al. .............. 260/294.8

*Primary Examiner*—Albert T. Meyers
*Assistant Examiner*—Daren M. Stephens
*Attorney, Agent, or Firm*—Sughrue, Rothwell, Mion, Zinn & Macpeak

[57] ABSTRACT

Pharmaceutical compositions containing 2-amino-6-benzyl-3-ethoxycarbonyl-4,5,6,7-tetrahydro-thieno[2,3-c]pyridine hydrochloride and a method of using such compositions in treatment of liver dysfunction in mammals are disclosed.

3 Claims, No Drawings

TREATMENT OF LIVER DYSFUNCTION WITH 2-AMINO-6-BENZYL-3-ETHOXYCARBONYL-4,5,6,7-TETRAHYDRO-THIENO[2,3-C]PYRIDINE HYDROCHLORIDE

BACKGROUND OF THE INVENTION

1. Field of the Invention

The present invention relates to pharmaceutical compositions containing 2-amino-6-benzyl-3-ethoxycarbonyl-4,5,6,7-tetrahydro-thieno-[2,3-c]pyridine hydrochloride, and to a method of using such compositions in treatment of liver dysfunction in mammals.

2. Description of the prior art

2-Amino-6-benzyl-3-ethoxycarbonyl-4,5,6,7-tetrahydro-thieno-[2,3-c]pyridine hydrochloride (hereinafter called tinoridine hydrochloride by generic name) of the formula

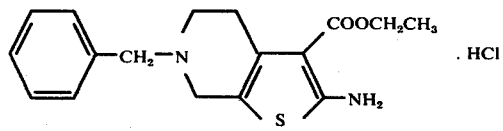

is disclosed in U.S. Pat. No. 3,563,997, and has utility as analgesic and antiinflammatory agent.

SUMMARY OF THE INVENTION

The present invention provides a new use for tincridine hydrochloride, namely the application of this agent to the treatment of liver dysfunction in mammals, e.g. in humans.

DETAILED DESCRIPTION OF THE INVENTION

The present invention has been accomplished on the basis of new finding that tinoridine hydrochloride shows highly protective effects on liver injuries of animals caused by carbon tetrachloride, thioacetamide and D-galactosamine. Such excellent pharmacological efforts are recognized as being indicative of effect in humans who are afflicted with liver dysfunction such as acute and chronic hepatitis, liver cirrhosis, fatty liver and toxic hepatitis induced by ethanol, organophosphorus insecticide, chloroform, carbon tetrachloride and so on. (see, for example, Arzneimittel-Forschung, vol. 18, 698 (1968) and vol. 21, 1194, 1209 (1971))

Protective effects of tinoridine hydrochloride on experimental disturbances in the rat liver are shown below:

I. Methods

1. Protective effect against acute liver injury by carbon tetrachloride

Essentially the test was performed according to the method described by Von G. Hahn et al. in "Arzneimittel-Forschung", vol. 18, 698 (1968).

Carbon tetrachloride ($CCl_4$) was dissolved in olive oil and injected intraperitoneally at a dose of 0.25 ml/kg to male Wistar rats (about 200 g). Then serum glutamic oxalacetic transaminase (S-GOT) and serum glutamic pyruvic transaminase (S-GPT) were determined by AutoAnalyser AA-II (Technicon Corporation) 24 hours after the $CCl_4$ injection. The test compound (tinoridine hydrochloride) was administered orally one hour before the $CCl_4$ injection. The results are shown in Table I.

2. Protective effect against acute liver injury by thioacetamide

The test was also performed essentially according to the method mentioned above.

Thioacetamide was dissolved in water and injected subcutaneously at a dose of 50 mg/kg to male Wistar rats (about 200 g). Then S-GOT and S-GPT activities were determined by AutoAnalyzer AA-II 24 hours after the thioacetamide injection. The test compound was administered orally one hour before the thioacetamide injection. The results are shown in Table II.

3. Protective effect against acute liver injury by D-galactosamine

Essentially the test was performed according to the method described by D. Keppler et al. in "Experimental and Molecular Pathology", vol. 9, 279 (1968). To Wistar rats (about 200 g) fasted for 24 hours, 100 mg of D-galactosamine in 1 ml of saline solution was injected intraperitoneally and 4 hours later an additional 50 mg of D-galactosamine in saline solution was injected. Then S-GOT and S-GPT activities were determined by AutoAnalyzer AA-II 7 hours after the initial injection of D-galactosamine. The test compound was administered twice orally each one hour before the D-galactosamine injection. The results are shown in Table III.

TABLE I

| Treatment | No. of Rats | S-GOT (mU/ml) | | S-GPT (mU/ml) | |
|---|---|---|---|---|---|
| Normal Control | 5 | 176±9** | (100) | 55±2** | (100) |
| $CCl_4$ Control | 5 | 2,848±646 | | 1,790±355 | |
| $CCl_4$ + Tinoridine Hydrochloride | | | | | |
| 10 mg/kg | 5 | 2,184±701 | (25) | 1,299±415 | (28) |
| 40 mg/kg | 4 | 1,274±147 | (59) | 666±110* | (65) |
| 160 mg/kg | 5 | 971±104* | (70) | 531±94* | (73) |

Mean ± S.E.
*p<0.05,
**p<0.01 vs. $CCl_4$ Control
The values parenthesized in Table I represent % inhibition.

TABLE II

| Treatment | No. of Rats | S-GOT (mU/ml) | | S-GPT (mU/ml) | |
|---|---|---|---|---|---|
| Normal Control | 4 | 180±11** | (100) | 66±4** | (100) |
| Thioacetamide Control | 6 | 1,818±268 | | 996±154 | |
| Thioacetamide + Tinoridine | | | | | |

TABLE II-continued

| Treatment | No. of Rats | S-GOT (mU/ml) | | S-GPT (mU/ml) | |
|---|---|---|---|---|---|
| Hydrochloride | | | | | |
| 25 mg/kg | 7 | 1,194±126* | (38) | 629±81* | (39) |
| 50 mg/kg | 6 | 889±181** | (57) | 488±102** | (55) |
| 100 mg/kg | 7 | 732±125** | (66) | 389±73** | (65) |
| 200 mg/kg | 7 | 798±89** | (62) | 425±54** | (62) |
| 400 mg/kg | 3 | 433±121** | (85) | 203±67** | (85) |

Mean ± S.E.
*p<0.05,
**p<0.01 vs. Thioacetamide Control
The values parenthesized in Table II represent % decrease vs. Thioacetamide Control.

TABLE III

| Treatment | No. of Rats | S-GOT (mU/ml) | | S-GPT (mU/ml) | |
|---|---|---|---|---|---|
| Normal Control | 5 | 139±3** | (100) | 42±2** | (100) |
| D-Galactosamine Control | 5 | 1,907±177 | | 1,141±134 | |
| D-Galactosamine + Tinoridine Hydrochloride | | | | | |
| 25 mg/kg × 2 | 5 | 1,218±159* | (39) | 627±99* | (47) |

Mean ± S.E.
*p<0.05
**p<0.01 vs. D-Galactosamine Control
The values parenthesized in Table III represent % decrease vs. D-Galactosamine Control.

In the histopathological studies, tinoridine hydrochloride has been found to improve necrosis, e.g. centrolobular necrosis caused by $CCl_4$, and focal necrosis caused by D-galactosamine.

The results of comparative studies of protective effect against liver injuries in rats by $CCl_4$ and thioacetamide are shown in Table IV. The testing methods are the same as mentioned above.

TABLE IV

| Test Compound | Dose mg/kg, p.o. | Protection %[a] of S-GPT | |
|---|---|---|---|
| | | $CCl_4$ | Thioacetamide |
| Tinoridine Hydrochloride | 50 | 65 | 43 |
| | 100 | 84 | 71 |
| Indomethacin | 2.5 | 21 | −11 |
| Phenylbutazone | 100 | 9 | 24 |
| Ibuprofen | 100 | −27 | 7 |
| Prednisolone | 10 | −26 | 84 |
| Clutathione | 250 (i.p.) | 31 | −62 |

[a]The percent inhibition is calculated by the following formula;
$\frac{b-c}{b-a} \times 100$
a: S-GPT activity of the normal
b: S-GPT activity of the control
c: S-GPT activity of the test compound As is seen from the data in Table IV, other known antiinflammatory agents (indomethacin, phenyloutazone, ibuprofen and prednisolone) and glutathione cannot be said to have very excellent protective affects on experimental liver injuries. Only tinoridine hydrochloride has quite potent effects.

In view of various tests, including those mentioned above, tinoridine hydrochloride can be safely administered for the treatment of liver dysfunction in mammals, e.g. in humans such as mentioned previously, in the form of a pharmaceutical preparation with a suitable and conventional carrier, without adversely affecting the patients.

The pharmaceutical preparation can take any conventional form of capsules, tablets and powders for oral administration, or of suppositories for topical administration. For example, 50 mg and 100 mg capsules are prepared from the following compositions:

| | 50 mg Capsules | 100 mg Capsules |
|---|---|---|
| Tinoridine Hydrochloride | 55.8 mg* | 111.6 mg** |
| Lactose | 50.0 | 50.0 |
| Starch | 42.0 | 35.0 |
| Methylcellulose | 1.2 | 2.0 |
| Magnesium Stearate | 1.0 | 1.4 |
| Total | 150.0 mg | 200.0 mg |

* equivalent to 50 mg of the base
** equivalent to 100 mg of the base

The daily dose of tinoridine hydrochloride for human adults suffering form liver dysfunction usually ranges from about 300 mg to 600 mg, i.e. 6 to 12 capsules, each capsule containing 55.8 mg. (equivalent to 50 mg of the base) of tinoridine hydrochloride, in single or multiple dose, but it may vary depending upon the age, body weight, and/or severity of the condition to be treated as well as the response to the medication.

Although the present invention has been adequately discussed in the foregoing specification, one readiy recognizes that various changes and modifications may be made without departing from the spirit and scope thereof.

What is claimed is:

1. A method for the treatment of liver dysfunction in mammals which comprises administering to said mammals an effective amount of 2-amino-6-benzyl-3-ethoxycarbonyl-4,5,6,7-tetrahydro-thieno-[2,3-c]pyridine hydrochloride.

2. A method of claim 1 wherein said effective dose comprises about 300 mg to about 600 mg to about 600 mg per day.

3. A method of claim 1 which comprises administering orally 6 to 12 capsules, each capsule containing 55.8 mg (equivalent to 50 mg of the base) of 2-amino-6-benzyl-3-ethoxycarbonyl-4,5,6,7-tetrahydro-thieno[2,3-c]pyridine hydrochloride.

* * * * *